Nov. 12, 1974 W. A. WARRINER Plant Pat. 3,652
ROSE PLANT
Filed May 16, 1973
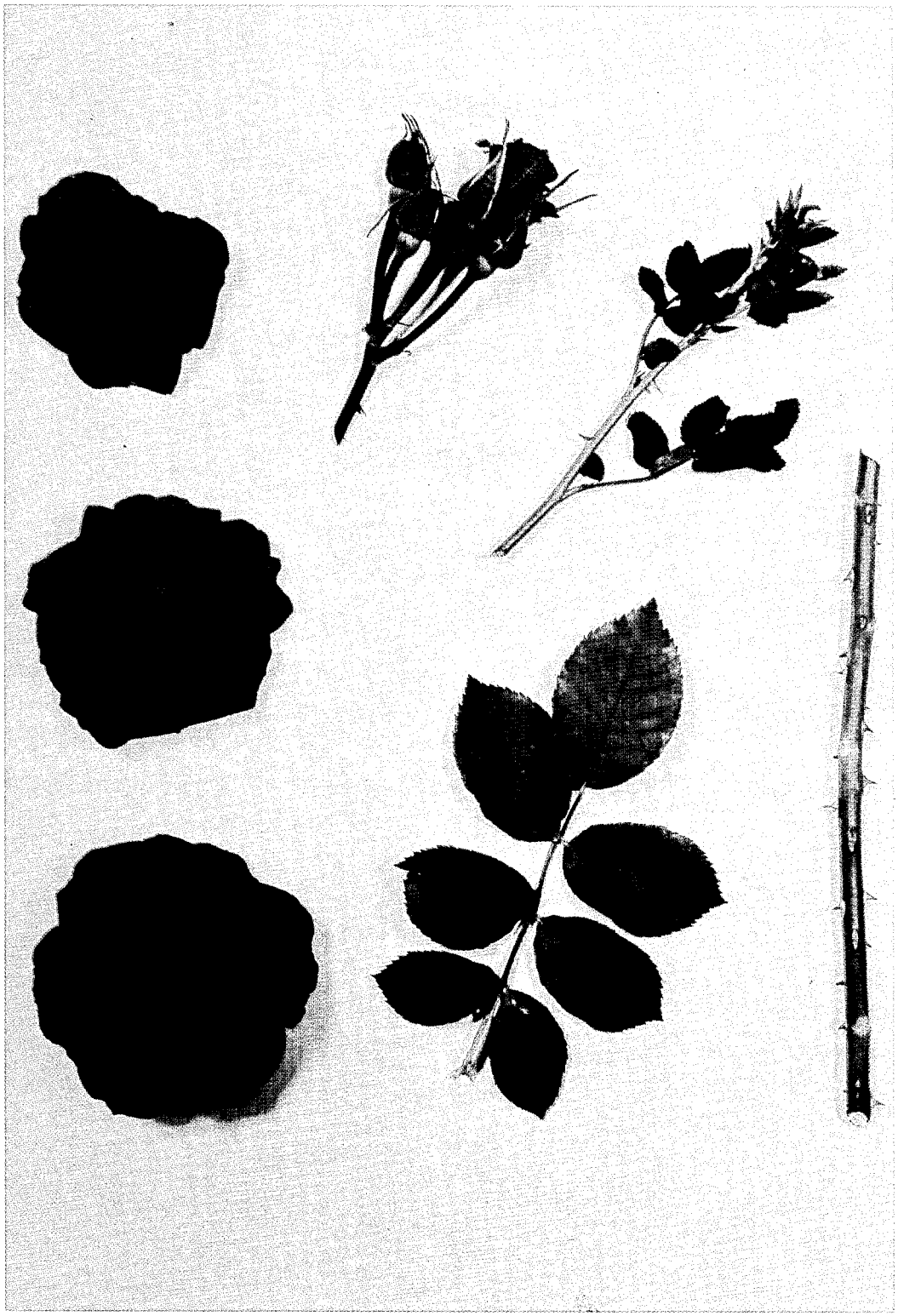

United States Patent Office

Plant Pat. 3,652

Patented Nov. 12, 1974

3,652

ROSE PLANT

William A. Warriner, Tustin, Calif., assignor to Jackson & Perkins Company, Medford, Oreg.

Filed May 16, 1973, Ser. No. 360,751

Int. Cl. A01h *5/00*

U.S. Cl. Plt.—6 1 Claim

The present invention relates to a new and distinct variety of rose plant of the climber class, which was originated by me by crossing the variety Climbing Ena Harkness with pollen from an unnamed variety.

This new variety of climbing rose plant has been named Tempo, which has been registered with the International Registration Authority for Roses, Columbus, Ohio.

The primary objective of this breeding was to produce a new and improved climbing type rose for garden use, which would bloom continuously throughout the growing season with blooms of large size and red color. This objective was fully achieved, along with other desirable features, as evidenced by the following unique combination of characteristics which are outstanding in the new variety and which distinguish it from its parents as well as from all other varieties of which I am aware:

1. A plant that produces blooms on the first flush of growth after planting on canes five to seven feet in length and then makes long, "climbing" canes ten to twelve feet in length which produce blooms on the terminals.

2. The long "climbing" canes produce blooms from lateral growth the same season in which the canes are produced as well as in following years.

3. During the second and subsequent years of growth, the lateral buds produce blooms early in the season and rebloom for the balance of the season which along with blooms on terminals of new canes gives a continuity of bloom over a relatively long growing season.

4. An attractive flower color of bright, nonbluing red near *Wilson's* Currant Red but somewhat brighter.

5. Flowers approximately 3½–4" in diameter of 45 to 50 petals.

6. Attractive, nearly glossy relatively large foliage.

Asexual reproduction of my new variety by budding as performed at Wasco, California, shows that the aforementioned characteristics and distinctions come true to form and are established and transmitted through succeeding propagations.

The accompanying drawing shows typical specimens of the vegetative growth and flowers of this new variety in different stages of development, and as depicted in color as nearly true as it is reasonably possible to make the same in a color illustration of this character.

The following is a detailed description of my new rose variety, with color terminology in accordance with *Wilson's Horticultural Color Chart,* except where a general color term of ordinary dictionary significance is indicated.

Parentage: Seedling.

*Seed Parent.*—Climbing Ena Harkness.

*Pollen Parent.*—Unnamed variety.

Classification:

*Botanic.*—Rosa hybrid.

*Commercial.*—Large flowered climber.

FLOWER

Observations were made at Irvine, California in mid April, 1973.

Blooming Habit: Intermittent. Blooms as bush first spring, then makes climbing canes which bloom on terminals.

Bud:

*Size.*—1¼–1½ inches when petals start to unfurl.

*Form.*—Ovoid to globular.

*Color.*—When sepals first divide Chrysanthemum Crimson (824). When half blown; inside of petals similar to Cardinal Red (822) but of a brighter tone, reverse of petals similar to Rose Red (724) but of a slightly darker tone.

*Sepals.*—Color: Outer surface Scheeles Green (860/1) overlaid in part with Garnet Brown (00918/3) or on some sepals entirely Garnet Brown (00918/3). Inner surface—Scheeles Green (860/2) with small hairs or tomentum. Three appendaged sepals lightly appendaged. Two unappendaged sepals hairy edged.

*Receptacle.*—Color: Scheeles Green (860/1) overlaid partly with Garnet Brown (00918/3). Shape: Upper part is cylindrical, lower part rounded. Size: Large. Surface: Smooth.

*Peduncle.*—Length: Short. Surface: Prickly. Color: Light green overlaid with Garnet Brown (00918/3). Strength: Stiff, erect.

*Opening.*—Outer petals roll back without pointing.

Bloom:

*Size.*—Medium. Average size when fully expanded 3½"–4".

*Borne.*—Singly and several together.

*Stems.*—Short, strong.

*Form.*—High center, outer petal edges slightly curled.

*Petalage.*—Number of petals under normal conditions 45–50.

*Color.*—Center of flower: Upper side of petals near Currant Red (821) but of a brighter tone. Reverse side of petals near Cherry (722/2). Outer petals: Upper side of petals same as center petals. Reverse of petals same as center petals. Base of petals small area near Primrose Yellow (601/3). General tonality from a distance Currant Red (821) but of a brighter tone.

*Discoloration.*—At end of third day near Cardinal Red (822/3). By sixth day between Cardinal Red (822) and Chrysanthemum Crimson (824).

*Fragrance.*—Very slight.

Petals:

*Texture.*—Medium thickness—stiff.

*Surface.*—Inside—satiny. Reverse—shiny.

*Shape.*—Round.

*Form.*—Tips slightly recurved.

*Arrangement.*—Informal (malformed in center). Petaloids in center; few.

*Persistence.*—Drop off cleanly.

*Lastingness.*—On the plant—very long. As a cut flower—very long.

Reproductive parts:

*Stamens, Anthers.*—Large. Color—yellow. Arrangement—regular around styles.

*Stamens, Filaments.*—Long. Color—near Signal Red (719/1) with yellow base.

*Pollen.*—Gold yellow.

*Stigmas.*—Color—yellow near Primrose Yellow (601/3).

*Ovaries.*—All enclosed in calyx.

PLANT

Form: Climber.

Growth: Very vigorous.

Foliage: Number of leaflets on normal mid-stem leaves, 5 or 7.

*Size.*—Medium.

*Quantity.*—Abundant.

*Color.*—New foliage: Near Garnet Brown (00918/3) until leaves open up, then changing quickly to old foliage color. Old foliage: Near Parsley Green (00962/1).

Leaflets:

*Shape.*—Oval, nearly elliptic.

*Texture.*—Upper side—semi glossy. Under side—smooth. Ribs and veins—ordinary.

*Edge.*—Serrated.

*Serration.*—Single, small.

*Petiole.*—Rachis—Color—green. Underside—few prickles.

*Disease Resistance.*—Susceptible to mildew during spring at Irvine, California.

Wood:

*New Wood.*—Color—garnet. Bark—Smooth.

*Old Wood.*—Color—green. Bark—smooth.

Prickles:

*Quantity.*—On main stalks—ordinary. On laterals—ordinary.

*Form.*—Broad base, medium, hooked slightly downward.

*Color.*—When young—brown.

*Position.*—Irregular.

Small prickles:

*Quantity.*—None.

I claim:

1. A new and distinct variety of rose plant of the climbing class, substantially as herein shown and described, characterized particularly as to novelty by the unique combination of an extremely vigorous and everblooming habit of growth; production of climbing canes which bloom on the terminals and later bloom on the lateral growth, a flower color of a brighter tone but near Wilson's Currant Red.

No references cited.

ROBERT E. BAGWILL, Primary Examiner